United States Patent [19]

Subramanyam et al.

[11] Patent Number: 5,435,933
[45] Date of Patent: Jul. 25, 1995

[54] COMPOSITION OF SYNTHETIC DETERGENTS

[75] Inventors: Ravi Subramanyam, North Brunswick; Jairajh Mattai, Methuchen; Ben Gu, East Brunswick, all of N.J.

[73] Assignee: Colgate-Palmolive Company, Piscataway, N.J.

[21] Appl. No.: 111,676

[22] Filed: Aug. 25, 1993

[51] Int. Cl.$^6$ ............... C11D 15/00; C11D 15/04; C11D 9/30; C11D 1/38
[52] U.S. Cl. .................... 252/108; 252/117; 252/121; 252/554; 252/555; 252/545; 252/546; 252/DIG. 16
[58] Field of Search ............... 252/117, 121, 554, 555, 252/108, DIG. 16, 545, 546

[56] References Cited

U.S. PATENT DOCUMENTS

| | | | |
|---|---|---|---|
| 2,749,315 | 6/1956 | Faler | 252/117 |
| 2,868,731 | 1/1959 | Henderson et al. | 252/117 |
| 3,070,547 | 12/1962 | Chaffee | 252/121 |
| 3,076,766 | 2/1963 | Anstett | 252/117 |
| 3,226,330 | 12/1965 | Anstett | 252/117 |
| 3,640,882 | 2/1972 | Groves et al. | 252/121 |
| 3,793,215 | 2/1974 | Smith | 252/117 |
| 3,835,058 | 9/1974 | White | 252/121 |
| 4,673,525 | 6/1987 | Small et al. | 252/132 |
| 4,812,253 | 3/1989 | Small et al. | 252/132 |
| 4,867,899 | 9/1989 | Ahmed et al. | 252/121 |
| 4,919,838 | 4/1990 | Tibbets et al. | 252/117 |
| 4,954,282 | 9/1990 | Rys et al. | 252/117 |
| 5,254,290 | 10/1993 | Blandiaux et al. | 252/545 |

OTHER PUBLICATIONS

Schoenberg, Formulating Mild Skin Cleansers, Soap/Cosmetics/Chemical Specialties for May 1983, pp. 33–37, 95.

Primary Examiner—Paul Lieberman
Assistant Examiner—Patricia L. Hailey
Attorney, Agent, or Firm—Martin B. Barancik; Robert C. Sullivan

[57] ABSTRACT

A composition comprising:
a. about 20 to 50 wt % of a long chain acyl monoglyceride sulfate salt, and
b. about 5 to 20 wt % of a sulfosuccinate of the formula

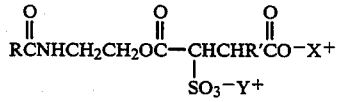

wherein R is alkyl or alkenyl of 8 to 22 carbon atoms, inclusive, R' is hydrogen or methyl and X and Y are the same or different and are alkali metal, ammonium or substituted ammonium cation.

11 Claims, No Drawings

COMPOSITION OF SYNTHETIC DETERGENTS

BACKGROUND OF THE INVENTION

Soaps have been utilized for many years to remove soil from the human body and fabrics. Although the irritation factor of soaps are of little or no consequence for use in fabric cleansing, the usage of various other detergents in personal care of mammals including humans is becoming of even greater significance. Synthetic detergents are used in combination with traditional soaps in various new body cleansing products. Various detergents include long chain sulfonates, sulfates, taurates, non-ionic detergents such as amides or amido compounds and cationic materials. These materials include, for example, specific sulfonate salts such as isethionates usually in the long chain acyl form such as the cocoyl moiety or as derivatives of glyceryl such as long chain alkyl glyceryl ether sulfonates. Combination bars utilizing the synthetic detergent and various quantities of soap have been successfully commercialized in materials known as "Dove" and "Oil of Olay". The search for further combinations of synthetic detergents which will bring about increased mildness to the skin of users of such cleansing formulations continues.

A new composition of synthetic detergents has been found which is unusually non-irritating to skin as well as maintaining excellent and in some cases even better detergency activity with respect to lathering characteristics compared to certain commercial formulations.

SUMMARY OF THE INVENTION

In accordance with the invention there is a personal care cleansing formulation comprising
a. about 20 to 50 wt % of a long chain acyl monoglyceride sulfate salt, and
b. about 5 to 20 wt % of a long chain alkyl or alkenyl monoethanol or isopropyl amine sulfosuccinate salt.

DETAILED DESCRIPTION OF THE INVENTION

The long chain acyl group of the monoglyceride sulfate salt has from about 8 to 22 carbon atoms, inclusive, preferably from about 10 to about 20 carbon atoms inclusive. Although these are usually saturated groups, there can be some olefin unsaturation, also present in the saturated group. The long chain groups are at least predominantly saturated which is preferred. Examples of the acyl groups, preferably normal, include caprylic, capric, lauric, myristic, stearic and the like. The salt group can be any alkali metal salt or any other cation which provides water solubility to the salts such as a ammonium or substituted ammonium salt such as triethanolamine or triethyl amine. Examples of the alkali metals include sodium and potassium. The monoglyceride sulfate salt is generally prepared by esterifying the monoglyceride sulfate salt with a long chain acid such as cocoyl acid or other naturally occurring acid which has a mixture of long chain fatty acids. The preferred composition of the monoglyceride sulfate salt is where the acyl group is derived from tallow or cocoyl or a mixture of tallow and cocoyl acids generally from about 70 to 85% coco and 15 to 30% tallow.

The second necessary surfactant is a monoester disalt sulfosuccinate of the formula

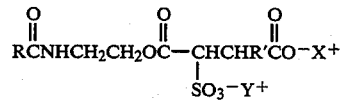

wherein R is alkyl or alkenyl of 8 to 22 carbon atoms, inclusive; R' is a hydrogen or methyl; X and Y are the same or different and are alkali metal, ammonium or substituted ammonium cation present in about 5 to 20 wt % of the composition.

Additional other material can also be present in the composition such as free fatty acids, soap and other surfactants. The composition is aqueous in nature and preferably consists essentially of a and b in bar or liquid form and more preferably consists essentially of a, b, and soap; a, b and free fatty acid or even more preferably consists essentially of a, b, soap and a free fatty acid.

The acyl monoglyceride sulfate salt is prepared by reacting a glyceride sulfate with a long chain fatty acid such as coco acid, tallow acid or combination thereof. Some unsaturation can be present in the acid, however is preferred that it be predominantly saturated hydrocarbon, i.e. alkyl. Acyl groups of from eight to twenty two carbon atoms are employed, preferably ten to twenty carbon atoms. Combinations of tallow and coco acid are in ranges of preferably about 60–80 wt % coco and 20 to 40 wt % tallow. Generally tallow acid is rich in $C_{16}$–$C_{18}$ alkyl groups and coco acid is rich in $C_{12}$ groups. The cations employed to form the salt are the standard ones such as alkali metals, i.e. sodium and potassium, ammonium, substituted ammonium such as triethylamine, triethanolamine and the like.

Quantities of component a in the composition are from about 20 to 50 wt %, preferably 25 to 45 wt %, more preferably 30 to 40 wt % of a. as measured by the composition weight.

Component b, the di salt monoester sulfsuccinate, of the formula is generally prepared by reacting a long chain acid with a monoethanolamine or monoisopropanol amine of a sulfosuccinate. The R group of the molecule is usually determined by the length the R group of the long chain fatty acid used in the synthesis. As stated before, R is methyl or hydrogen, preferably hydrogen.

The quantities of component b in the composition are from about 5 to 20 wt %, preferably from about 8 to 15 wt %.

The quantity of soap, that is, long chain alkyl or alkenyl, preferably alkyl or alkyl with small quantities of alkenyl carboxylate salts, is generally from about 2 to 15 wt % of the composition when soap is present. When present it is preferably from about 5 to 12 wt % of the composition.

Free fatty carboxylic acids can also be present in the composition. Generally these acids are from about 8 to 22 carbon atoms, inclusive, and are generally alkyl but may have some olefinic unsaturation therein. Preferred are fatty acids from about 10 to 20 carbon atoms such as lauryl, myristyl, palmitic, stearic and the like. When present the free fatty acid is about 10 to 30 wt % of the composition, preferably about 15 to 25 wt %.

Other material may be in the composition such as moisture (water), colorants, fragrances, inorganics and the like. The form of the cleansing agent may be solid, (bar-like), liquid or gel like to deliver the cleansing components.

Other surfactants may be present in the composition as long as the irritation and detergency of the composition are not adversely affected, for example small quantities of SCI and AGES can also be present.

It has been found that the addition of relatively small quantities of component b., the sulfosuccinate, to the acyl monoglyceride sulfate, surprisingly bring about increased mildness while still maintaining detergency such as lathering foam quality, quantity and rapidity of foaming which can be better than conventionally used synthetic detergents such as sodium cocoylisethionate (Lever Brothers, Dove Bar) also known as SCI and alkyl glyceryl ether sulfonate (Proctor and Gamble, Oil of Olay) also known as AGES which is equivalent to or better than various combination bars and synthetic detergents commercially available.

In order to properly evaluate mildness of these various combination bars and synthetic detergents, the sensitivity of the collagen swelling assay was increased. The regular collagen swelling assay is recognized as an in vitro predictor of clinical irritation. The value of the increased sensitivity collagen swelling assay was demonstrated in an in vivo soap chamber test which verified the higher sensitivity collagen assay as a positive predictor of clinical irritation among various synthetic detergent compositions.

The modified collagen swelling assay was performed in the following manner.

40 ml of a 1% solution of syndet bar, or its reformulated actives, is prepared from millipore water. This stock solution is spiked with tritium labelled water to give about 25,000 cpm/ml, i.e., approximately 1,000,000 cpm/40 ml.

Six pieces of collagen (Colla-Tec, Inc. NJ) each weighing 15-25 mg (weighed to the fifth decimal place), are weighed into scintillation vials. Five milliliters of the tritium labelled product solution are added to each vial. The vials are incubated for 48 hours at 50° C. After incubation, the collagen pieces are removed and rapidly rinsed in a large volume of water (about 1 liter) to remove excess soap and/or label on the film surface. Each swollen piece of collagen is digested with 1 ml of 2M NaOH for about 1 hour at 70° C., until the solution is clear. The vials are then cooled to room temperature, 10 ml of scintillation cocktail (Ecolume (ICN Biochemicals)) and 200 microliter of concentrated perchloric acid are added, and the vials are vortexed to give a clear solution. The tritium concentration in the vials are then counted. The collagen swelling values (ml of water uptake/g collagen) are calculated using the dpm values and known activity of the stock solution (determined by measuring the dpm/ml of the stock solution, in triplicate). Comparison of collagen swelling values, and therefore predicted irritation potential, between samples are done using an analysis of variance (ANOVA).

The increased sensitivity of the assay comes from increasing the weight of the usual collagen sample, increasing the concentration of the radiolabeled material, increasing the incubation time and increasing the number of samples of collagen.

Utilizing this modified collagen swelling assay two commercial synthetic detergent bars, Dove and Oil of Olay, were reproducibly distinguishable. The data is presented in ml of water (swelling) per g. of collagen. The higher the number, the more irritating to skin is the tested composition.

TABLE 1

Reproducibility of the modified collagen swelling values (ml/g collagen) for Dove versus Oil of Olay.

| Sample | Swelling | | |
|---|---|---|---|
| | Expt 1 | Expt 2 | Expt 3 |
| Dove | 8.14 ± 0.35 | 5.95 ± 0.22 | 7.75 ± 0.37 |
| Oil of Olay (white) | 6.94 ± 0.15 | 5.11 ± 0.18 | 6.79 ± 0.28 |

Oil of Olay is demonstratably less irritating than Dove in this test system.

In Table 2 below, the skin irritability of a number of synthetic detergents was measured. As used in this Table and throughout the remainder of the data, TCMGS is tallow coco monoglyceride sodium salt wherein the coco is 75 wt % and the tallow is 25 wt % of the acyl grouping. MEA is monoethanolamide.

TABLE 2

Collagen swelling (ml/g collagen) of pure surfactants (1%)

| Surfactant | Swelling |
|---|---|
| SCI* | 8.52 ± 0.30 |
| TCMGS | 8.31 ± 0.29 |
| Lauryl sarcosinate | 7.28 ± 0.22 |
| AGES-$^a$ 23, pure | 6.94 ± 0.37 |
| AGES$^b$ 45, pure | 6.93 ± 0.09 |
| Cocamido MEA sulfosuccinate | 5.91 ± 0.37 |
| AGES$^b$ (Oil of Olay) | 5.54 ± 0.13 |

*sodium cocoylisethionate [an a, b, alkyl glyceryl ether sulfonate]
$^{a, b}$alkyl glyceryl ether sulfonate of differring alkyl chain lengths.

As shown in this Table, TCMGS alone is the equivalent of SCI in skin irritability for these synthetic detergents.

However as shown in Table 3 below, the addition of a sulfosuccinate of component b brings about a significant reduction in skin irritancy.

TABLE 3

Collagen swelling (ml/g collagen) of 1% solutions of various synthetic detergent systems.

| Sample | Swelling |
|---|---|
| 40% T/CMGS/10% rincinoleamido MEA sulfosuccinate/X | 5.36 ± 0.30 |
| 30% T/CMGS/20% rincinoleamido MEA sulfosucinate/X | 4.83 ± 0.24 |
| 40% T/CMGS/10% cocamido MEA sulfosuccinate/X | 5.38 ± 0.57 |
| 30% T/CMGS/20% cocamido MEA sulfosuccinate/X | 4.84 ± 0.47 |
| Oil of Olay | 6.55 ± 0.22 |

(X = 20.5% fatty acid (41/59) 10% soap (85/15)/5% NACl)

Interestingly, the effect of the combination of a and b together of the invention composition is far greater than would be expected from their individual values as shown in Table 2. In fact, together they are less irritating in their composition than Oil of Olay.

Below are the chemical compositions of Oil of Olay and the 10 wt % cocamido MEA sulfosuccinate composition. As is observed, the compositions are appropriate for comparison testing and observations.

TABLE 4

Composition of Oil of Olay, White

| Component | Wt Percent White |
|---|---|
| Moisture | 3 |
| NaCl | 4 |
| $TiO_2 + Na_2SO_4$ | 2 |
| Free Fatty Acid (M.W. = 242) | 16 |

TABLE 4-continued

Composition of Oil of Olay, White

| Component | Wt Percent White |
|---|---|
| Soap (M.W. = 264) | 8 |
| Na Sarcosinate (M.W. = 292) | 12 |
| AGES*(M.W. = 357) | 48 |
| Fragrance (Est.) | 1 |
| Free oil (nonionic) | 5 |

*alkylglycerylethersulfonate

TABLE 4A

Composition of T/CMGS/10% CASS* syndet bars**

| Component % | 10 |
|---|---|
| TCGMS | 44 |
| Coco monoglyceride sulfate | 10 |
| CASS*** | 10 |
| DDBS**** | 2 |
| soap (85/15) tallow/cocoa | 13 |
| stearic acid | 23 |
| EDTA | 0.02 |
| BHT | 0.02 |
| $Na_2SO_4$ | 4 |
| Free Oil | 1 |
| $TiO_2$ | 0.50 |
| Opacifier | 1 |
| Moisture | 1 |

(***CASS—Cocamido MEA Sulfosuccinate)
(****DDBS—Sodium Dodecyl Benzene Sulfonate)

When the superior mildness composition of the invention in Table 3 are tested for their physical properties in Table 5, the suitability of the 20 wt % upper limitation of the sulfosuccinate is noted.

TABLE 5

Performance Evaluation of T/CMGS/CASS Syndet Bars

| | Example 1 | Example 2 | Example 3 | Example 4 |
|---|---|---|---|---|
| MEA Na Cococyl Sulfosuccinate wt % | 10 | 15 | 20 | 0 |
| Moisture % | 2.26 | 1.47 | 3.87 | 2.45 |
| Hardness (mm) | 2.21 | 1.72 | 2.50 | 2.18 |
| Slough % | 20.09 | 20.89 | 24.95 | 17.61 |
| Use-Up % (× 20) | 26.07 | 28.24 | 29.52 | 24.64 |
| Processability | Fair | Slightly Difficult | Difficult | Easy |

In Table 6 below, the lathering properties of the 10 wt % sodium cococyl MEA sulfosuccinate composition of the invention was tested against the 0 wt % material (all T/CMGS) and commercial Oil of Olay by 20 panelists in a study. 19 of the 20 panelists preferred the composition of the invention, example 1, over Oil of Olay.

TABLE 6

Magnitude Estimation of Lather of Syndet Bars (20 panelists)

| Score | Lather Quickness | Quality | Quantity | Total |
|---|---|---|---|---|
| Example 1 10 wt% component b | 7.13 | 8.07 | 8.15 | 23.31 |
| Example 4 0 wt% component b | 6.43 | 6.73 | 6.58 | 19.74 |
| Oil of Olay | 6.08 | 6.58 | 6.28 | 18.94 |

The composition of the invention out performed Oil of Olay in overall lathering and in each of the subcategories of quickness, quality and quantity of lather. The higher the number, the better the lathering characteristics.

Utilizing the well known inverse cylinder method of measuring foaming, the net values for 0.4 wt %, 0.2 wt % and 0.1 wt % composition solutions in deionized (DI) water and water with 100 ppm hardness were measured after stopping of mixing (initial) and 5 minutes thereafter.

Below are the results.

TABLE 7

Net foam value of T/CMGS/sulfosuccinate syndet bars (cylinder method)

| Concentration | Example 1 10 wt% component b Initial/5 min. | Example 3 20 wt% component b Initial/5 min. | Example 4 0 wt% component b Initial/5 min. |
|---|---|---|---|
| 0.4% DI* | 473  403 | 413  361 | 440  365 |
| 0.2% DI* | 378  320 | 300  245 | 328  255 |
| 0.1% DI* | 268  195 | 200  143 | 220  150 |
| 0.4% 100 ppm** | 325  250 | 275  217 | 265  188 |
| 0.2% 100 ppm** | 253  183 | 212  149 | 235  170 |
| 0.1% 100 ppm** | 210  130 | 133   98 | 195  125 |

*DI—Deionized water solution.
**100 ppm—100 ppm hardness solution.

The example of the invention out performed the 100% T/CMGS. The composition with 20 wt % sulfosuccinate was the poorest foaming performer further providing additional reason for not having greater than 20 wt % of sulfosuccinate in the composition.

The compositions of this invention have significantly increased mildness to the skin than the competitive commercial product while maintaining excellent foaming properties and good processing characteristics.

We claim:

1. A personal cleansing composition in bar form comprising:
   a. about 20 to 50 wt % of a long chain acyl monoglyceride sulfate salt, said acyl having from about 8 to 22 carbon atoms, and
   b. about 5 to 20 wt % of a sulfosuccinate of the formula

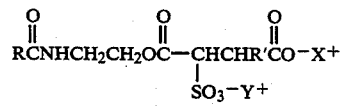

wherein R is alkyl or alkenyl of 8 to 22 carbon atoms, inclusive, R' is hydrogen or methyl and X and Y are the same or different and are alkali metal, ammonium or substituted ammonium cation.

2. The composition in accordance with claim 1 wherein a is about 25 to 45 wt %.

3. The composition in accordance with claim 1 wherein b is about 8 to 15 wt %.

4. The composition in accordance with claim 1 wherein soap is also present.

5. The composition in accordance with claim 1 wherein free fatty acid is also present.

6. The composition in accordance with claim 5 wherein soap is about 2 to 15 wt % of the composition.

7. The composition in accordance with claim 6 wherein free fatty acid is about 10 to 30 wt % of the composition.

8. The composition in accordance with claim 1 wherein soap is present in about 2 to 15 wt % and free fatty acid is present in from about 10 to 30 wt % of the composition.

9. A method for cleansing human skin which comprises applying to human skin a composition defined in claim 1.

10. A personal cleansing composition in bar form consisting essentially of:
   a. about 20 to 50 wt % of a long chain acyl monoglyceride sulfate salt, said acyl having about 8 to 22 carbon atoms and
   b. about 5 to 20 wt % of a sulfosuccinate of the formula

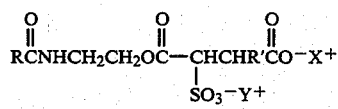

wherein R is alkyl or alkenyl of 8 to 22 carbon atoms, inclusive, R' is hydrogen or methyl and X and Y are the same or different and are alkali metal, ammonium or substituted ammonium cation.

11. The method for cleansing human skin which comprises applying to human skin a composition defined in claim 10.

* * * * *